US008067629B2

(12) United States Patent
Tong

(10) Patent No.: US 8,067,629 B2

(45) Date of Patent: Nov. 29, 2011

(54) DISPERSANT ANTIFOULANT FOR ACRYLONITRILE

(75) Inventor: David Youdong Tong, Houston, TX (US)

(73) Assignee: Nalco Company, Naperville, IL (US)

( * ) Notice: Subject to any disclaimer, the term of this patent is extended or adjusted under 35 U.S.C. 154(b) by 424 days.

(21) Appl. No.: 12/274,036

(22) Filed: Nov. 19, 2008

(65) Prior Publication Data

US 2010/0125147 A1 May 20, 2010

(51) Int. Cl.
*C07C 255/00* (2006.01)

(52) U.S. Cl. ........................................ 558/462

(58) Field of Classification Search .................. 558/462
See application file for complete search history.

(56) References Cited

U.S. PATENT DOCUMENTS 3,691,226 A 9/1972 Halvorsen et al.
4,902,824 A 2/1990 Syrinek
5,650,072 A * 7/1997 Mc Clain et al. ............ 210/698
5,746,924 A * 5/1998 Cooper et al. ............... 210/698

OTHER PUBLICATIONS

A. V. R. Reddy et al., "Surface modification of ultrafiltration membranes by preadsorption of a negatively charged polymer—I. Permeation of water soluble polymers and inorganic salt solutions and fouling resistance properties," *Journal of Membrane Science*, vol. 214, Apr. 2003, pp. 211-221.

T. Murosaki. et al., "Antifouling activity of synthetic polymer gels against cyprids of the barnacle (*Balanus amphritrite*) in vitro,"*Biofouling*, vol. 25, No. 4, May 2003, pp. 313-320.

Raphael Trouillon et al., "Comparative study of poly(styrene—sulfonate)/poly(L-lysine) and fibronection as befouling-preventing layers in dissolved oxygen electrochemical measurements,"Analyst, *Royal Society of Chemistry*, GB, vol. 134, No. 4, Jan. 2009, pp. 794-793.

* cited by examiner

*Primary Examiner* — Rei-tsang Shiao

(74) *Attorney, Agent, or Firm* — Benjamin E. Carlsen; Michael B. Martin

(57) ABSTRACT

A styrene sulfonate polymer which is highly effective at preventing fouling of equipment used in the manufacturing process of acrylonitrile. The styrene sulfonate polymer is particularly effective when introduced into the quench column, the recovery stage and the wastewater processing section of the acrylonitrile manufacturing process.

18 Claims, 3 Drawing Sheets

17
3
18
4
23
24
11
28
12
28
29

DISPERSANT ANTIFOULANT FOR ACRYLONITRILE

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to a process for the preparation of acrylonitrile and, more particularly, to a process wherein an antifoulant comprising a polymer of styrene sulfonate is added to at least one step in the quench, the recovery and the wastewater process of an acrylonitrile manufacturing process.

Typically, the manufacture of acrylonitrile comprises three stages, the reaction stage, the recovery stage, and the purification stage. In the reaction stage, propylene undergoes ammoxidation to form acrylonitrile by reaction with ammonia and oxygen. This often is a gas-phase catalytic reaction at an elevated temperature. The resulting acrylonitrile-containing effluent is then quenched with water and unreacted ammonia is neutralized with sulfuric acid. In the recovery stage the quenched product of the reaction stage undergoes a water absorption process to capture acrylonitrile and a recovery process to separate the acrylonitrile from water and other heavy components that also formed during the reaction stage. Water is recycled within the recovery stage. Recovered acrylonitrile is then passed on to the purification stage.

During the recovery stage fouling compounds tend to form and collect in the recycled water. The fouling compounds include both inorganic and organic compounds in the form of monomers, oligomers, prepolymers, and polymers in various combinations. These fouling compounds form deposits along some of the recovery stage equipment such as heat exchangers, reboilers, and columns. When deposited on the heat exchange surfaces of the heat exchangers and reboilers, the fouling compounds reduce the efficiency of heat transfer equipment. Furthermore, the deposition of foulant creates flow resistance through effected equipment, and even causes blockages in the process flow. As a result, periodically the equipment has to be shut down in order to remove the foulant, which results in production loss, cleaning expenditure, operation inconvenience, as well as related safety and environment issues.

Known methods of addressing this problem include adding a dispersant antifoulant to problematic equipment. The dispersant functions as a colloidal stabilizer which keeps foulant suspended in the process stream and prevents foulant from becoming deposited on equipment surfaces. One such example is disclosed in U.S. Pat. No. 3,691,226 which describes the use of lignosulfonate metal salts to minimize foulant deposition on the heat transfer surface of the heater exchangers used to cool recycled water. Another example is U.S. Pat. No. 5,650,072 which teaches the use of naphthalene sulfonate formaldehyde condensate polymer to prevent fouling of heat exchangers in an acrylonitrile stripper.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §. 1.56(a) exists. All patents and patent applications cited within this application are hereby incorporated by reference in their entirety.

BRIEF SUMMARY OF THE INVENTION

At least one embodiment of the invention is directed to a method for mitigating or eliminating the fouling problem in the quench and the recovery stages of manufacturing acrylonitrile by introducing a styrene sulfonate polymer dispersant antifoulant having a repeating unit formula according to Formula I:

Formula I

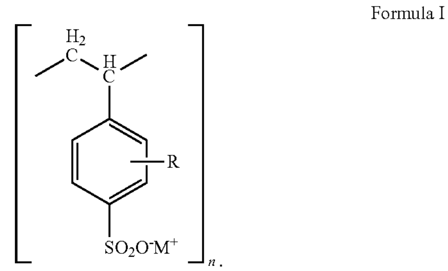

This dispersant prevents the fouling compounds from depositing on the quench and recovery stage equipment. Experimental data has proven that the dispersant is superior to the prior art.

BRIEF DESCRIPTION OF THE DRAWINGS

A detailed description of the invention is hereafter described with specific reference being made to the drawings in which.

DETAILED DESCRIPTION OF THE INVENTION

Figure 1:
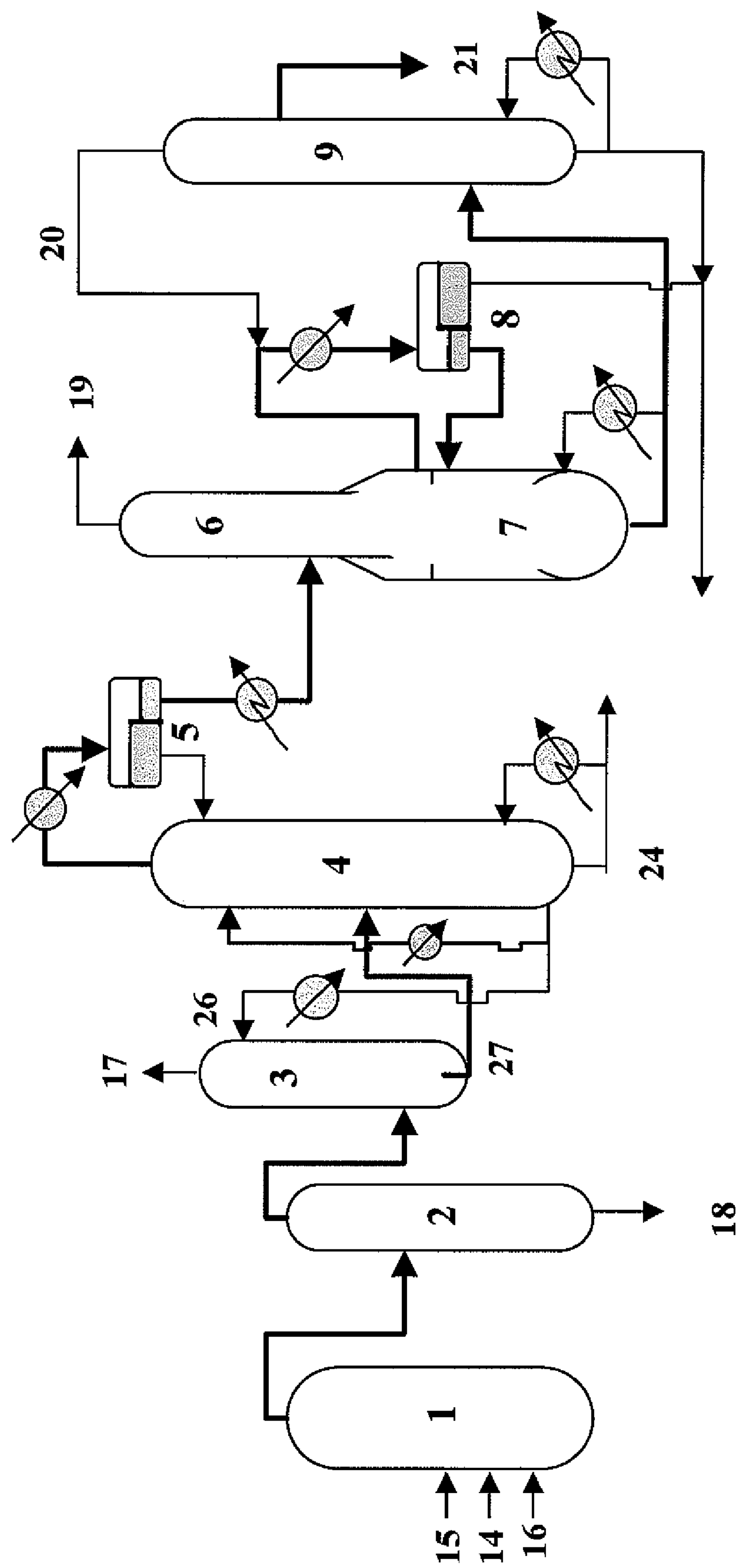
FIG. 1 is a general illustration of the manufacturing process of acrylonitrile in which the inventive dispersant is used.

Referring now to FIG. 1 there is shown a general illustration of the three common stages of the manufacture of acrylonitrile process that the inventive dispersant is added to. A person of skill in the art would recognize that there are many variations known in the manufacturing process of acrylonitrile and FIG. 1 is representative of these known variations. The three stages are the reaction stage (25), the recovery stage (24), and the purification stage (23). In the reaction stage (25), input propylene (15) reacts with oxygen or air (16) and ammonia (14) within a reactor (1) during an ammoxidation reaction to form acrylonitrile. The reaction effluent then passes on to a quench tower (2) where it is quenched with circulation water (18), and where unreacted ammonia is neutralized with sulfuric acid. Following the quench operation the products pass on to the recovery stage where the products enter an absorber column (3). In the absorber column (3), acrylonitrile and heavy components are scrubbed with lean water (26) from light components (such as $O_2$, CO, $CO_2$, and unreacted propylene etc.). The acrylonitrile-containing absorber bottom, known as rich water (27), is sent to the recovery column (4), while the light components are off gassed (17) through the top of the absorber column (3) and incinerated.

In the recovery column (4), the rich water undergoes extraction distillation. Acrylonitrile and hydrogen cyanide are taken off through an overhead portion of the recovery column (4) along with their azeotropes and water. The majority of the water coming with the rich water stream is taken out of the lower section of the recovery column (4) and recycled as lean water to the absorber column (3). Solvent water passes on to the overhead portion as well. A small portion of the water from the recovery column (4) is purged through the bottom of the recovery column (4), and it is either sent back to the quench column or to a waste water process for disposal. In FIG. 1, the recovery column distillation operation is sustained by reboiler heat exchangers associated with the recovery column (4).

The acrylonitrile bearing stream in the overhead portion then passes on to the purification stage (23) where hydrogen cyanide (19), water (20), and heavy materials are separated from the acrylonitrile product (21). The purification stage (23) comprises a recovery overhead decanter (5), heads column (6), dry column (7), heads/dry decanter (8) and product column (9). More information on the ammoxidation reaction to form acrylonitrile can be found in U.S. Pat. No. 3,691,226.

For purposes of this application the definition of rich water is water that passes from the absorber column to the recovery column and is concentrated in acrylonitrile. For purposes of this application, lean water is what remains after the rich water has passed down a recovery column and no longer has acrylonitrile in it. Lean water is recycled back into the absorber column and passes down the column in a counter-current flow relative to the off-gassed components. For purposes of this application, solvent water (26) is what remains after the rich water that has also passed down a recovery column and therefore no longer has acrylonitrile in it. The solvent water is fed into the recovery column top section to reduce contamination of the acrylonitrile stream that passes into the decanter (5).

Figure 2:
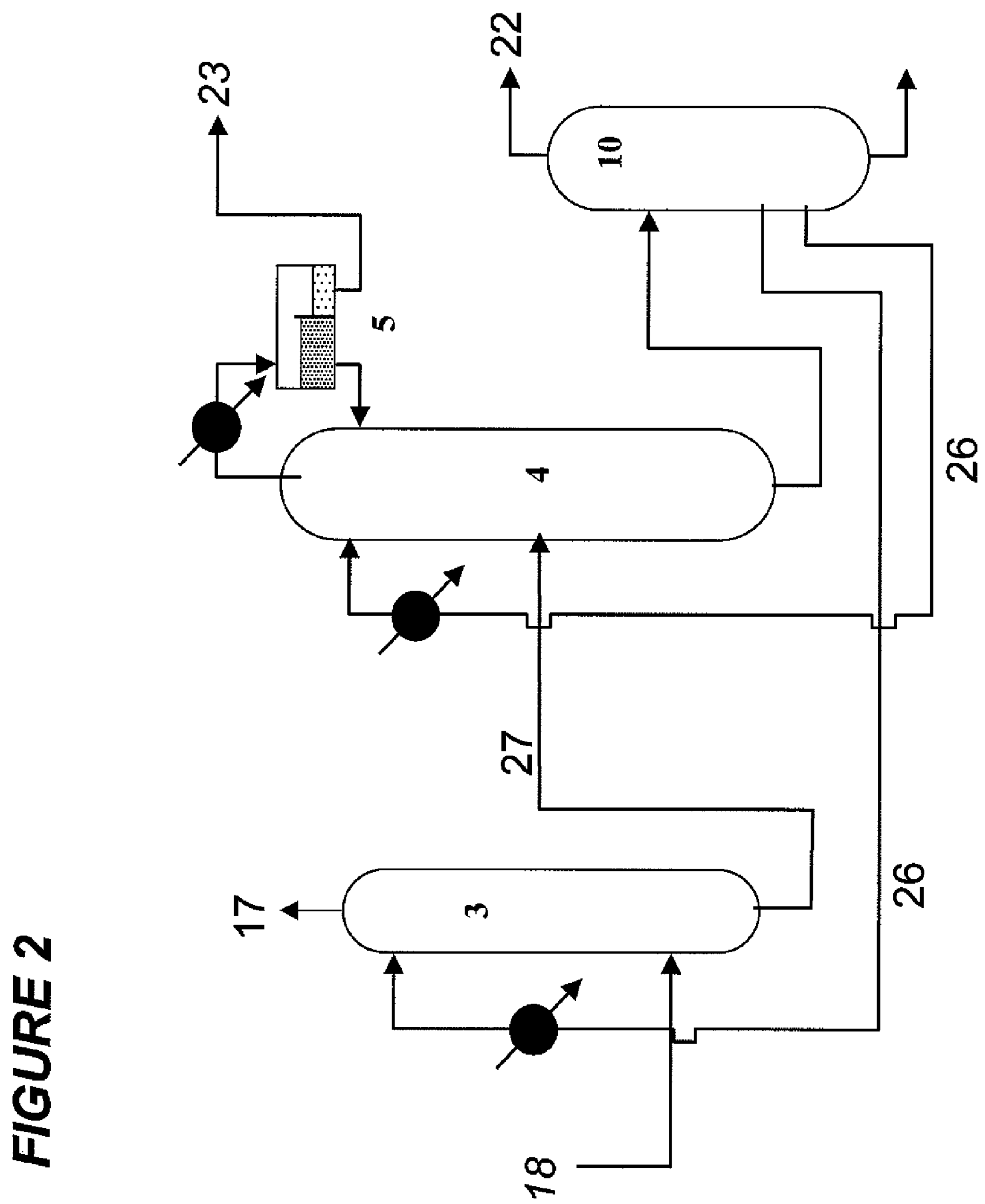
FIG. 2 is a more detailed illustration of one design in a recovery stage of acrylonitrile manufacture in which the inventive dispersant is used.
Figure 3:
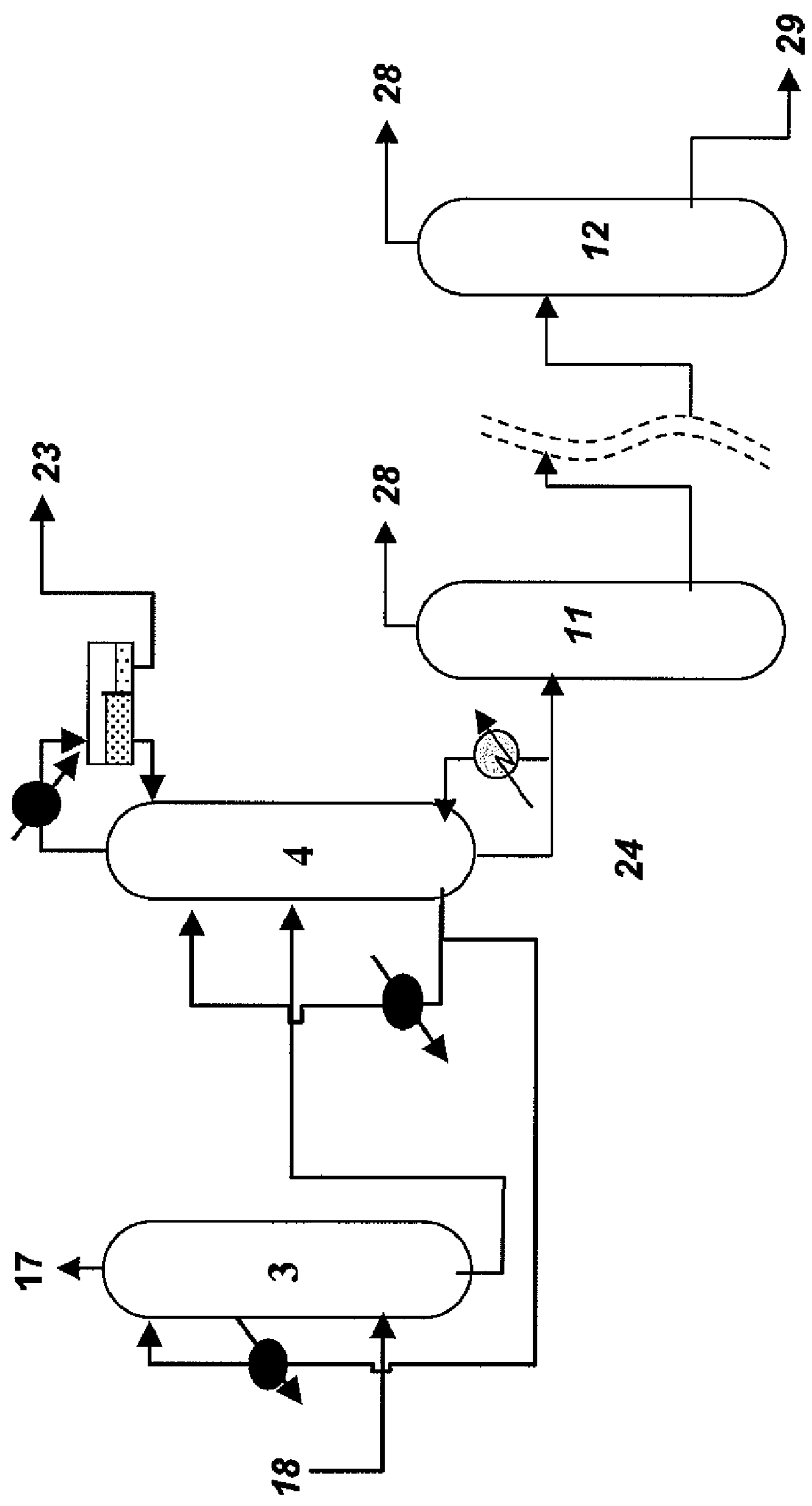
FIG. 3 is a more detailed illustration of another design in a recovery stage of acrylonitrile manufacture in which the inventive dispersant is used.

Variation in design is very common among acrylonitrile plants. FIGS. 2 and 3 show two different designs in the recovery and wastewater handling. In the FIG. 2 design, a separate stripping column (10) is added, which strips off acetonitrile (22) and light components from the solvent water (26). In FIG. 3, a multistage evaporation wastewater process (11 and 12) is used to strip water off the recovery bottom purge stream in order to minimize wastewater disposal. The overhead water (28) is recycled back to quench, and the bottom (29) is sent to the wastewater treatment facility.

As lean water and solvent water recycle through the recovery stage and the recovery bottom purge goes through the stripper column or through a multistage wastewater distillation, they undergo various physical and chemical changes that result in foulants forming in various components, vessels, and equipment of the recovery stage as well as the wastewater process. For purposes of this application the definition of the term foulant is a material deposit that accumulates on equipment during the operation of a manufacturing and/or chemical process which may be unwanted and which may impair the operation and/or efficiency of the process. Foulant accumulation impedes and blocks liquid throughput in particular through recovery columns. Foulant is especially detrimental when it accumulates along the heat exchangers which cool the lean and the solvent water, and the reboilers or strippers because the foulant's poor thermal conductivity causes these components to become less efficient.

At least one embodiment of the invention is the addition of a styrene sulfonate polymer into one or more of the fluid streams of the acrylonitrile manufacturing process. The styrene sulfonate polymer is a polymeric material comprising the following repeating units:

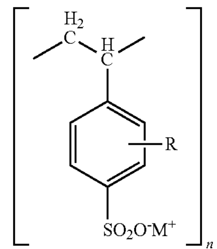

wherein M is hydrogen, alkali metals or ammonium or a mix of them, R is hydrogen, alkyl aryl, alkylaryl, arylalkyl, R may contain heteroatoms, n is an integer.

In at least one embodiment the styrene sulfonate polymer is introduced into one or more of the fluid streams of the quench column and the recovery stage as well as the wastewater process where it acts as a dispersant that prevents foulant deposition and even facilitates the removal of previously deposited foulant. Previous examples of dispersants used in various manufacturing processes include: sulfonated oils, sulfonated fatty acids, sulfated oils, sulfated fatty acids, naphthalene sulfonate formaldehyde, sulfonic acids, dodecylbenzene sulfonic acid, and lignosulfate metal salts (as described in U.S. Pat. Nos. 5,650,072, 4,650,072, 5,746,924, and 3,691,226). Experimental data however, proves that in the recovery stage of acrylonitrile manufacture, styrene sulfonate polymer has superior dispersant properties over all of these previous dispersants.

At low pH and/or higher contamination concentration where prior art dispersants tend to become ineffective, the styrene sulfonate polymer provides superior dispersion performance. In at least one embodiment the dispersant has a molecular weight of 50,000 to 2,000,000 Dalton. In at least one embodiment the dispersant has a molecular weight of at least 100,000 to 1,000,000 Dalton.

There are a number of ideal locations in the quench, the recovery stage and the wastewater process fluid circuits where the styrene sulfonate polymer dispersant can be introduced. These include, but are not limited to, the circulation streams of the quench column, the lean water circuit before the lean water cooler exchanger, the solvent water circuit before or after the solvent water cooler exchanger, the feed line to the reboiler, the feed to the stripper column and the feed to the multistage distillation wastewater process. In particular, introduction of the dispersant immediately prior to a heat exchanger or reboiler is effective because it provides intact and sufficient amounts of dispersant to the exchanger or reboiler. The effective dosage ranges from 1 to 10,000 ppm by weight, depending upon fouling severity and treatment economics. In practice, a preferred dosage ranges from 5 to 1000 ppm, and the most preferred dosage is from 10 to 200 ppm.

The styrene sulfonate polymer dispersant by itself is generally present as solid, and a solvent is generally used to dissolve it and to prepare a liquid formulation. This is generally done when the styrene sulfonate polymer is made. Though styrene sulfonate polymer is soluble in many solvents, water is the solvent most often used for obvious reasons. For economic consideration, highly concentrated styrene sulfonate polymer formulation is generally desirable. Co-solvents may be used with water to enhance solubility and improve product stability and handling.

The following examples are presented to describe embodiments and utilities of the invention and are not meant to limit the invention unless otherwise stated in the claims.

EXAMPLES

Example 1A

Dispersion Test Simulating the Solvent Water Cooler Fouling

A sample of foulant deposit material was taken from the recovery solvent water cooling exchanger of an acrylonitrile plant. The foulant sample was dried and ground into powder. A foulant solution was prepared by dissolving the foulant powder in an organic solvent. In a 15 mL volume centrifugal tube, 15 mL of the recovery column solvent water stream of a recovery column from the same acrylonitrile plant was added. 1 mL of the above prepared foulant solution was added to the centrifugal tube. The content in the tube was well shaken and then the tube was allowed to stand at ambient temperature. Precipitation was seen in the tube. After 2.5 hours about 0.5 mL of precipitate was recorded at the bottom of the tube.

Example 2A

Sample Treated with the Inventive Styrene Sulfonate Polymer

The same procedure as in Example 1A was performed except that before adding the foulant solution, the contents of the tube were dosed with 39 ppm of the invention styrene sulfonate polymer. This tube did not show any precipitation during the 2-day period of this experiment. This example demonstrates that the inventive styrene sulfonate polymer is an effective dispersant for the fouling situation.

Example 3A

Sample Treated with Prior Art Dispersants

The same procedure as in Example 1A was performed except that before adding the foulant solution, the contents of the tube were dosed with 57 ppm of a naphthalene sulfonate polymer. Precipitation did not occur until 20 hours of the settlement. Three days later about 0.2 mL solid precipitate was measured at the bottom of the tube. The naphthalene suflonate polymer is effective only to a certain degree toward this fouling situation.

Example 1B

Dispersion Test Simulating Recovery Bottom Fouling

A sample of foulant deposit material was taken from the recovery reboiler of an acrylonitrile plant. The foulant sample was dried and ground into powder. A foulant solution was prepared by dissolving the foulant powder in an organic solvent. In a 15 mL volume centrifugal tube, 15 mL of the bottom purge stream of a recovery column from the same acrylonitrile plant was added. This recovery column bottom stream contained a higher concentration of contaminates and exhibited a lower pH than the solvent water stream. An aliquant of the above prepared foulant solution was added to the same centrifugal tube. The tube contents were shaken well and then the tube was allowed to stand at ambient temperature. Precipitation occurred in less than 5 minutes. After 30 minutes about 3 mL precipitate was recorded at the bottom of the tube.

Example 2B

Sample Treated with Styrene Sulfonate Polymer

The same procedure as in Example 1B was performed except that before adding the foulant solution, the tube content was dosed with 39 ppm of the inventive styrene sulfonate polymer. This tube did not show any precipitation during the 3-day period of this experiment. This example demonstrates that the inventive styrene sulfonate polymer is an effective dispersant for fouling situations.

Example 3B

Sample Treated with Prior Art Dispersants

The same procedure as in Example 1B was performed except that before adding the foulant solution, the tube contents were dosed with 57 ppm of a naphthalene sulfonate polymer. Precipitation occurred after a few minutes. After 30 minutes about 3 mL precipitate was recorded at the bottom of the tube. The naphthalene suflonate polymer is ineffective toward this fouling situation.

Example 1C

Dispersion Test Simulating Fouling of the Recovery Reboiler

A sample of foulant deposit material was taken from the recovery column reboiler of an acrylonitrile plant. The foulant sample was dried and ground into powder. A foulant solution was prepared by dissolving the foulant powder in an organic solvent. In a 10 mL volume centrifugal tube, 8 mL of the recovery column bottom purge stream from an acrylonitrile plant was added. 2 microliters of glacial acetic acid was added to the content to lower its pH. 50 microliters of the above prepared foulant solution was added to the same centrifugal tube. The tube was well shaken and then the tube was allowed to stand at elevated temperatures. At about 70° C., precipitation occurred in the untreated tube.

Example 2C

Sample Treated with Prior Art Lignosulfonate Dispersant

The same procedure as in Example 1C was performed except that before adding the foulant solution, the tube contents were dosed with 39 ppm of a lignosulfonate dispersant. This tube did not show any precipitation at 70° C. However, precipitation was observed when the temperature was raised to 90° C. This example demonstrates the limited effectiveness of the lignosulfonate dispersant.

Example 3C

Sample Treated with Prior Art Naphthalene Sulfonate Resin Dispersant

The same procedure as in Example 1C was performed except that before adding the foulant solution, the tube was dosed with 57 ppm of a naphthalene sulfonate polymer. No precipitation was seen at 70 and 90° C. Then, an additional 3 microliters of acetic acid was added to the content. Immediately, precipitation was observed. This example shows that the naphthalene suflonate polymer has limited dispersion effect toward this fouling situation.

Example 4C

Sample Treated with the Invention Styrene Sulfonate Polymer Dispersant

The same procedure as in Example 3C was performed except that the tube content was treated with 57 ppm of the inventive styrene sulfonate polymer dispersant. No precipitation was seen at 70 and 90° C. No precipitation was observed either with the addition of 3 microliters of acetic acid. This example demonstrates that the styrene suflonate polymer is a more effective dispersant toward this fouling situation than prior art.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of preventing foulant deposition in the manufacturing process of acrylonitrile which comprises:

(i) cooling gas phase reactants from an amoxidation reaction of propylene, the gas phase reactants from an amoxidation reaction comprising nitrogen, acrylonitrile, hydrogen cyanide, acetonitrile, carbon dioxide, carbon monoxide, propylene, water, oxygen, acrolein, ammonia, carboxylic acids, aldehydes, and nitriles, (ii) passing the cooled gas phase reactants countercurrent to an aqueous stream of acid to neutralize ammonia present in the cooled gas phase reactants, (iii) recovering the ammonia from the gas phase reactants, (iv) contacting the remaining gas phase reactants with water to form a fluid phase of the manufacturing process, and (v) adding to the fluid phase of the manufacturing process an effective antifouling amount of styrene sulfonate polymer having the following repeating unit formula:

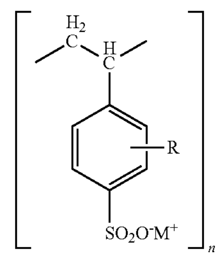

wherein M is hydrogen, alkali metals or ammonium or a mixture of them, R is hydrogen, alkyl, aryl, alkylaryl, arylalkyl, R may contain heteroatoms, and n is an integer with a value greater than 10.

2. The method of claim 1 in which the fluid phase is from the ammoxidation reaction of propylene, ammonia and oxygen (and/or air).

3. The method of claim 1 in which the manufacturing process further comprises that the styrene sulfonate polymer is added to an item selected from the list consisting of: a recovery stage, a water recycling pipeline, a multistage distillation wastewater process, a quench column, a heat exchanger, a reboiler, and a stripper and any combination thereof, at least one selected item being in sealable fluidic communication with the other items.

4. The method of claim 1 in further comprising a quench column which cools the ammoxidation reactor effluent with a circulating aqueous stream and the styrene sulfonate polymer is added to the circulating aqueous stream.

5. The method of claim 1 further comprising a recovery stage which itself comprises at least one absorber and at least one, recovery column, all in sealable fluid communication with each other, in the absorber rich water with a high concentration of acrylonitrile is formed through absorption by lean water, in the recovery column acrylonitrile is recovered by distillation separation, the styrene sulfonate polymer is added to at least one item selected from the list consisting of the absorber column and the recovery column.

6. The method of claim 1 further comprising at least one recycle water pipe line which takes water from one portion of the manufacturing process and recycles it by transferring it to another portion of the manufacturing process, the styrene sulfonate polymer is added to the recycle water pipe line.

7. The method of claim 6 in which the water transferred by the recycle water pipe line comprises solvent water which is circulated to the top of a recovery column and the styrene sulfonate polymer is added to solvent water.

8. The method of claim 6 in which the water transferred by the recycle water pipe line comprises lean water and the styrene sulfonate polymer is added to lean water.

9. The method of claim 1 in further comprising a wastewater processing section which processes the purge stream from the recovery column bottom through a multistage distillation operation and the styrene sulfonate polymer is added to the feed to the waste water processing section.

10. The method of claim 1 in which the styrene sulfonate polymer has a molecular weight of 50,000 to 2,000,000.

11. The method of claim 1 in which the styrene sulfonate polymer has a molecular weight of 100,000 to 1,000,000.

12. The method of claim 1 the styrene sulfonate polymer is added at a dosage of 1 to 10,000 ppm.

13. The method of claim 1 the styrene sulfonate polymer is added at a dosage of 10 to 1000 ppm.

14. The method of claim 1 the styrene sulfonate polymer is added at a dosage of 20 to 200 ppm.

15. The method of claim 1 the styrene sulfonate polymer is used in combination with other antifoulants, such as dispersants and polymerization inhibitors, corrosion inhibitors, antifoams, either by injecting separately or together.

16. The method of claim 1 in which the styrene sulfonate polymer is a solid dissolved in a solvent.

17. The method of claim 16 further comprising a co-solvent.

18. The method of claim 16 in which the solvent is water.

* * * * *